(12) United States Patent
Miller et al.

(10) Patent No.: US 7,867,255 B2
(45) Date of Patent: Jan. 11, 2011

(54) SPINAL ROD CONNECTOR SYSTEM AND METHOD FOR A BONE ANCHOR

(75) Inventors: Keith E. Miller, Germantown, TN (US); William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 921 days.

(21) Appl. No.: 11/399,927

(22) Filed: Apr. 7, 2006

(65) Prior Publication Data

US 2007/0270805 A1    Nov. 22, 2007

(51) Int. Cl.
 *A61B 17/70* (2006.01)
 *A61B 17/88* (2006.01)

(52) U.S. Cl. ............ 606/250; 606/260; 606/279

(58) Field of Classification Search ............ 606/60, 606/246, 250–262, 264–265, 267, 270–272, 606/278–279, 300–302, 305, 319, 328; 623/17.11; 403/388–391, 396
See application file for complete search history.

(56) References Cited

U.S. PATENT DOCUMENTS

| | | | |
|---|---|---|---|
| 4,361,141 A | 11/1982 | Tanner | |
| 4,771,767 A | 9/1988 | Steffee | |
| 4,773,402 A | 9/1988 | Asher et al. | |
| 4,854,304 A | 8/1989 | Zielke | |
| 5,053,034 A | 10/1991 | Olerud | |
| 5,154,718 A | 10/1992 | Cozad et al. | |
| 5,217,461 A | 6/1993 | Asher et al. | |
| 5,330,472 A | 7/1994 | Metz-Stavenhagen | |
| 5,330,473 A | 7/1994 | Howland | |
| 5,330,474 A * | 7/1994 | Lin ............ | 606/267 |
| 5,336,223 A | 8/1994 | Rogers | |
| 5,344,422 A * | 9/1994 | Frigg ............ | 606/278 |
| 5,403,314 A * | 4/1995 | Currier ............ | 606/278 |
| 5,425,732 A | 6/1995 | Ulrich | |
| 5,486,174 A | 1/1996 | Fournet-Fayard et al. | |
| 5,487,744 A * | 1/1996 | Howland ............ | 606/264 |
| 5,534,001 A | 7/1996 | Schlapfer et al. | |
| 5,536,268 A * | 7/1996 | Griss ............ | 606/254 |
| 5,562,660 A | 10/1996 | Grob | |
| 5,571,102 A * | 11/1996 | Cavagna et al. ............ | 606/250 |
| 5,575,790 A | 11/1996 | Chen et al. | |
| 5,593,408 A | 1/1997 | Gayet et al. | |
| 5,630,816 A * | 5/1997 | Kambin ............ | 606/252 |
| 5,643,260 A | 7/1997 | Doherty | |
| 5,658,284 A | 8/1997 | Sebastian et al. | |
| 5,716,355 A * | 2/1998 | Jackson et al. ............ | 606/252 |

(Continued)

FOREIGN PATENT DOCUMENTS

EP    0 612 507 A1    2/1994

(Continued)

*Primary Examiner*—Thomas C Barrett
*Assistant Examiner*—Larry E Waggle, Jr.

(57) ABSTRACT

A spinal rod system includes a first rod and a second rod engaged to a connector with the first and second rods extending axially therefrom in opposite directions from one another. The connector is mountable to a mounting anchor and securable thereto with an engaging member. The connector secures the first rod in the mounting anchor and the connector is clampingly engaged between the engaging member and the first rod. The second rod is engageable in a receiving portion of the connector adjacent to the mounting anchor.

36 Claims, 5 Drawing Sheets

U.S. PATENT DOCUMENTS

| | | | |
|---|---|---|---|
| 5,735,852 A * | 4/1998 | Amrein et al. | 606/278 |
| 5,741,255 A * | 4/1998 | Krag et al. | 606/264 |
| 5,743,907 A * | 4/1998 | Asher et al. | 606/264 |
| 5,876,403 A * | 3/1999 | Shitoto | 606/308 |
| 5,888,221 A * | 3/1999 | Gelbard | 623/17.11 |
| 5,928,233 A * | 7/1999 | Apfelbaum et al. | 606/261 |
| 5,993,449 A * | 11/1999 | Schlapfer et al. | 606/60 |
| 6,099,528 A | 8/2000 | Saurat | |
| 6,102,912 A | 8/2000 | Cazin et al. | |
| 6,106,527 A | 8/2000 | Wu et al. | |
| 6,171,311 B1 | 1/2001 | Richelsoph | |
| 6,231,575 B1 * | 5/2001 | Krag | 606/264 |
| 6,241,730 B1 | 6/2001 | Alby | |
| 6,264,658 B1 * | 7/2001 | Lee et al. | 606/254 |
| 6,328,739 B1 * | 12/2001 | Liu et al. | 606/264 |
| 6,328,741 B1 | 12/2001 | Richelsoph | |
| 6,520,962 B1 | 2/2003 | Taylor et al. | |
| 6,551,318 B1 * | 4/2003 | Stahurski | 606/252 |
| 6,676,661 B1 | 1/2004 | Benlloch et al. | |
| 6,682,529 B2 * | 1/2004 | Stahurski | 606/301 |
| 6,685,705 B1 | 2/2004 | Taylor | |
| 7,645,294 B2 * | 1/2010 | Kalfas et al. | 606/250 |
| 2003/0045878 A1 * | 3/2003 | Petit et al. | 606/61 |
| 2004/0087949 A1 * | 5/2004 | Bono et al. | 606/61 |
| 2004/0220575 A1 | 11/2004 | Biedermann et al. | |
| 2004/0267264 A1 * | 12/2004 | Konieczynski et al. | 606/73 |
| 2005/0154388 A1 | 7/2005 | Roussouly et al. | |
| 2005/0171537 A1 | 8/2005 | Mazel et al. | |
| 2005/0228376 A1 | 10/2005 | Boomer et al. | |
| 2005/0228378 A1 * | 10/2005 | Kalfas et al. | 606/61 |
| 2005/0277932 A1 * | 12/2005 | Farris | 606/61 |
| 2006/0079892 A1 * | 4/2006 | Roychowdhury et al. | 606/61 |

FOREIGN PATENT DOCUMENTS

| | | |
|---|---|---|
| EP | 0 584 803 A1 | 3/1994 |
| WO | WO 94/26190 | 11/1994 |
| WO | WO 03/037200 | 5/2003 |

\* cited by examiner

SPINAL ROD CONNECTOR SYSTEM AND METHOD FOR A BONE ANCHOR

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment, in correcting abnormal curvatures and alignments of the spinal column, and for treatment of other conditions.

While external rod systems have been employed along the vertebrae, the geometric and dimensional features of these rod systems and patient anatomy constrain the surgeon during surgery and prevent optimal placement and attachment along the spinal column. For example, elongated, one-piece rods can be difficult to maneuver into position along the spinal column, and also provide the surgeon with only limited options in sizing and selection of the rod system to be placed during surgery. Accommodation of post-operative anatomical changes in the patient can also present challenges.

SUMMARY

According to one aspect, a spinal rod system includes a mounting anchor including a first portion for engaging a bony structure and a receiver defining a first receptacle. A first elongated spinal rod is positioned in the receptacle of the mounting anchor. A connector includes a body extending along a longitudinal axis that is oriented transversely to the first spinal rod. The body includes a mounting portion and a receiving portion along the longitudinal axis. The mounting portion is positioned about the receiver and engaged thereto with an engaging member. The receiving portion is positioned adjacent the receiver of the mounting anchor and defines a second receptacle. A second spinal rod can be engaged in the second receptacle of the receiving portion of the connector and extends from the receiving portion in generally parallel relation with the first spinal rod.

According to yet another aspect, a spinal rod system includes a mounting anchor including a first portion for engaging a bony structure and a receiver defining a first receptacle. A first elongated spinal rod is positioned in the receiver of the mounting anchor. A connector includes a body extending along a longitudinal axis and oriented transversely to the first spinal rod. The body includes a mounting portion and a receiving portion along the longitudinal axis. The mounting portion is positioned about the receiver and is clampingly engaged between the first spinal rod and an engaging member engaged to the receiver of the mounting anchor. The receiving portion of the connector body also defines a second receptacle adjacent the mounting portion. A second spinal rod can be engaged to the receiving portion of the connector in the second receptacle so that the second spinal rod extends from the receiving portion in generally parallel relation with the first spinal rod.

According to another aspect, a method for assembling a spinal rod system comprises: positioning a first spinal rod into a first receptacle defined by a receiver of a mounting anchor; positioning a mounting portion of a connector body about the receiver of the mounting anchor; securing an engaging member to the receiver of the mounting anchor with a flange of the engaging member in contact with the connector body and the connector body in contact with the first spinal rod outside the first receptacle; advancing the engaging member into the receiver thereby advancing the connector body and spinal rod in contact therewith until the spinal rod is seated against the receiver of the mounting anchor; and engaging a second spinal rod to the connector body.

According to one aspect, a spinal rod system includes a mounting anchor including a first portion for engaging a bony structure and a receiver defining a first receptacle. A first elongated spinal rod is positioned in the receptacle of the mounting anchor. A connector includes a body extending along a longitudinal axis that is oriented along the first spinal rod. The body includes a mounting portion and a receiving portion along the longitudinal axis. The mounting portion is positioned about the receiver and engaged thereto with an engaging member. The receiving portion is positioned adjacent the receiver of the mounting anchor and defines a second receptacle. A second spinal rod can be engaged in the second receptacle of the receiving portion of the connector and extends from the receiving portion in generally end-to-end and axial alignment with the first spinal rod.

According to yet another aspect, a spinal rod system includes a mounting anchor including a first portion for engaging a bony structure and a receiver defining a first receptacle. A first elongated spinal rod is positioned in the receiver of the mounting anchor. A connector includes a body extending along a longitudinal axis that extends in the same direction as and way from an end of the spinal rod in the receiver of the mounting anchor. The body includes a mounting portion and a receiving portion along the longitudinal axis. The mounting portion is positioned about the receiver and is clampingly engaged between the first spinal rod and an engaging member engaged to the receiver of the mounting anchor. The receiving portion of the connector body also defines a second receptacle adjacent the mounting portion. A second spinal rod can be engaged to the receiving portion of the connector in the second receptacle so that the second spinal rod extends from the receiving portion in a generally aligned and end-to-end relation with the first spinal rod.

These and other aspects will be apparent from the description that follows.

DESCRIPTION OF THE ILLUSTRATED EMBODIMENTS

Figure 1:
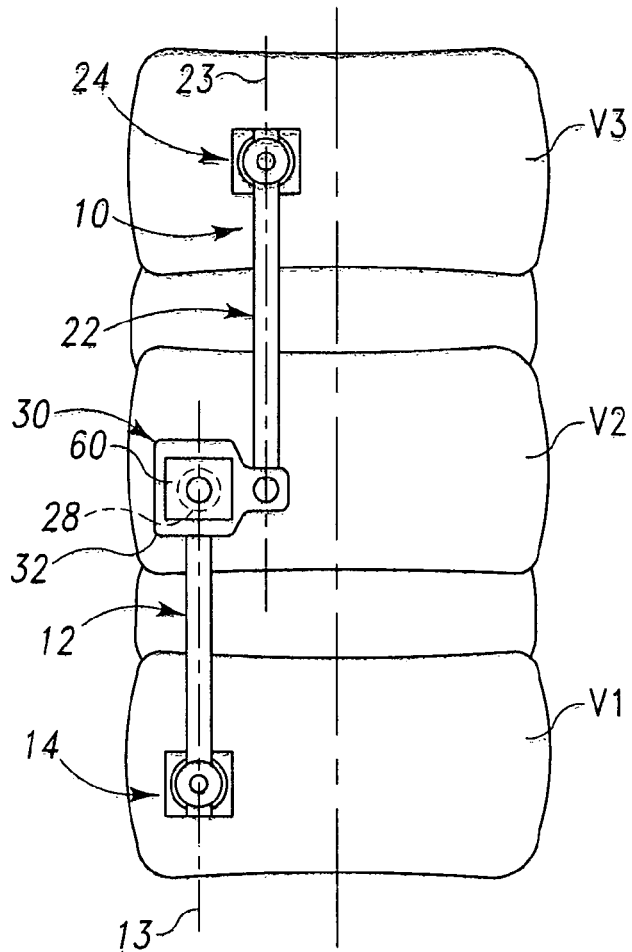
FIG. 1 is an elevation view of a spinal column segment shown diagrammatically and one embodiment of a stabilization system employing a connector to connect two rods to an anchor.

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein are contemplated as would normally occur to one skilled in the art to which the invention relates.

In FIG. 1 there is shown a spinal rod system 10 including a first rod 12 and a second rod 22. First rod 12 and second rod 22 are releasably coupled to one another with connector 30 at a mounting anchor 28 with rods 12, 22 in laterally offset and axially extending relation to one another when positioned along the spinal column. Rods 12, 22 provide a construct between the respective first and second vertebrae V1 and V2 and the respective second and third vertebrae V2 and V3 to provide a desired stabilization effect. First rod 12 can be secured to at least one vertebra V1 with at least one first anchor 14, and second rod 22 can be secured to at least one third vertebra V3 with at least one third anchor 24. Rods 12, 22 are secured to second, mounting anchor 28 engaged to vertebra V2 to provide a spinal rod system 10 along vertebrae V1, V2, V3.

The length of the construct between anchors 14 and 28 and anchors 24 and 28 can be decreased or increased by adjusting the axial positioning of one or more of the rods 12, 22 in the respective mounting anchor 28 and/or rod connector 30. Such adjustment may be desirable, for example, to provide an optimal fit during surgery, to allow rods of shorter length to be assembled in a single system, to allow rods of varying properties to be employed in the same system, and/or to adjust the length of the construct as a result of growth or other changes in the patient anatomy after the initial implantation procedure. In addition, system 10 can be adapted to extend along a single vertebral level, two vertebral levels as shown, or along three or more vertebral levels. System 10 can employ multiple mounting anchors and connectors along with multiple other anchors to secure two or more rods along the spinal column.

Connector 30 includes a connector body 32 releasably engageable to mounting anchor 28 and second rod 22. In addition, connector body 32 is positionable in contact with first rod 12 in mounting anchor 28 to secure first rod 12 to mounting anchor 28. Body 32 of connector 30 also includes a receptacle 44 for receiving second rod 22 therein. Connector 30 is configured to secure rods 12, 22 with rod 12 along rod axis 13 and rod 22 along rod axis 23. Axes 13, 23 can be generally parallel and offset from one another while minimizing the footprint or intrusiveness of the connector into the tissue surrounding the rod system and allowing the length of the rod construct for positioning and/or attachment along the spinal column to be readily adjustable. The rods 12, 22 can extend along their respective axes 13, 23 in opposite directions from rod connector 30 for positioning along one or more spinal motion segments of the spinal column to provide stabilization.

Figure 2:
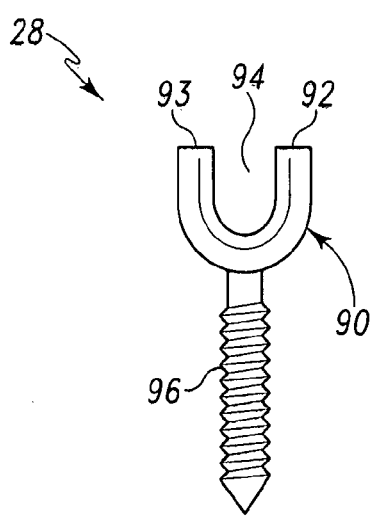
FIG. 2 is an elevation view of one embodiment of an anchor engageable with a vertebral body of the spinal column segment.
Figure 3:
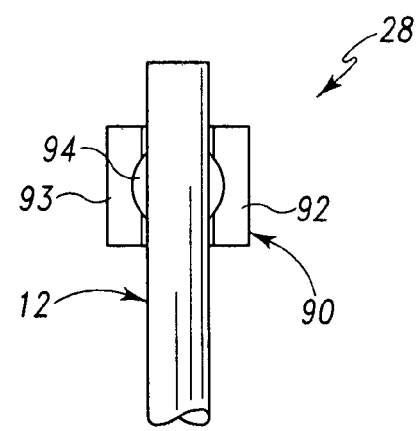
FIG. 3 is a plan view of the anchor of FIG. 2 with a spinal rod positioned in the anchor.

As shown in FIGS. 2-3, one embodiment for mounting anchor 28 is a bone screw with a tulip or U-shaped receiver 90 to receive rod 12 therethrough. Receiver 90 includes a pair of arms 92, 93 defining internal threads there along to threadingly engage an engaging member, such as engaging member 60 shown in FIG. 6. Arms 92, 93 define a receptacle 94 therebetween through which one of the rods 12, 22 can extend, such as shown with respect to rod 12. A bone engaging portion 96 extends distally from receiver 90 and can include an elongated shaft-like structure with external threads configured to threadingly engage bony tissue of a vertebral body. Other forms for bone engaging portion 96 are also contemplated, including hooks, staples, pins, spikes, wires, cables, sutures or other structure engageable to a vertebral body. In addition, anchor 28 is shown with bone engaging portion 96 fixed relative to receiver 90. Other forms contemplate bone engaging portion 96 is pivotal relative to receiver 90 in any one or combination of uni-planar, multi-axial, cone-shaped or otherwise configured pivot paths and orientations. For example, bone engaging portion 96 can include a head pivotally captured in receiver 90. Anchors 14 and 24 can be configured similarly to anchor 28, or may include any suitable configuration for securing a spinal rod along the spinal column.

Connector body 32 includes a receiving portion 38 for receiving rod 22 therein and a mounting portion 40 alongside receiving portion 38 for positioning about mounting anchor 28. Connector body 32 extends along a longitudinal axis 34 that is transversely oriented to rods 12, 22 when rods 12, 22 are engaged to connector body 32. The width of connector body 32 transverse to longitudinal axis 34 can be less than, the same as, or greater than the length along longitudinal axis 34. In addition, the width transverse to longitudinal axis 34 can vary along its length.

Figure 7:
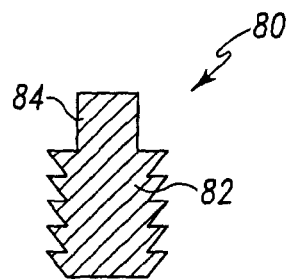
FIG. 7 is a section view of a second engaging member for coupling a rod to the connector.

Mounting portion 40 includes a length and width along and transverse to longitudinal axis 34 to accommodate receiver 90 of anchor 38 in window 50. Receiving portion 38 includes a length along axis 34 sufficient to form receptacle 44 for receiving rod 22 therein along a rod axis 23. Receiving portion 38 also includes a bore 42 for receiving an engaging member, such as engaging member 80 shown in FIG. 7, to secure rod 22 in position in receptacle 44.

In the illustrated embodiment, engaging member 80 is a set screw type member with a threaded body 82 threadingly engageable to internal threads along bore 42. A tool engaging portion 84 may be provided for engagement with a driving tool. Tool engaging portion 84 may be in the form of a proximally extending member as shown integrally formed with body 82, or may be in the form of an internal tool recess in body 82. Tool engaging portion 84 can be severable on application of a threshold torque to engaging member 80 when body 82 is positioned in contact with rod 22 in receptacle 44. Tool engaging portion 84 can also be fixed and non-removable from body 82.

Receiving portion 38 can include a depth d1 from a proximal or upper surface 48 of connector body 32 that positions the centerline of rod 22 in alignment distally and proximally with the depth d2 of the centerline of rod 12 below proximal surface 48. Other embodiments contemplate that depth d1 and depth d2 differ from one another to accommodate, for example, changes in the anatomy of the patient.

Figure 6:
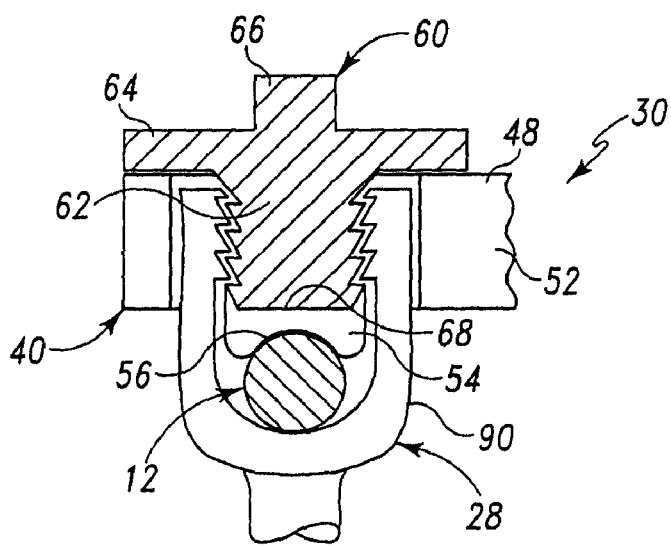
FIG. 6 is a section view of a first engaging member for coupling the connector to the anchor.

Mounting portion 40 of connector body 32 includes a central window 50 to receive receiver 90 of anchor 28 therein, as shown in FIG. 6. Wall 52 extends around window 50 and is shaped like the outer perimeter of anchor 28 so that receiver 90 is received in close, form-fitting engagement therewith. At least one contact member 54 extends distally from or is formed with wall 52 and is positioned in contact with rod 12 outside receptacle 94. Contact member 54 includes a distal contact surface 56 that can be concavely curved to fit around a portion of the convexly curved perimeter of rod 12. It is contemplated that a contact member 54 can be provided on each side of anchor 28 to contact rod 12 outside receptacle 94. The distal contact surface can include any suitable configuration, including configurations that conform to or extend around rods with non-circular outer perimeters.

Engaging member 60 is engageable to anchor 28 in receiver 90 with a threaded body portion 62. Body portion 62 includes at least one flange 64 extending outwardly therefrom that can contact connector body 32 along proximal surface 48 to force contact member 54 into contact with rod 12. As engaging member 60 is threadingly advanced into receiver 90, rod 12 is seated against receiver 90 by contact members 54 pressing thereagainst, limiting or preventing further rotation of engaging member 60. Thus, connector body 32 is clamped between flange 64 and rod 12.

In the illustrated embodiment, engaging member 60 is a set screw type member with threaded body 62 threadingly engageable to internal threads along arms 92, 93 of receiver 90. A tool engaging portion 66 may be provided for engagement with a driving tool. Tool engaging portion 66 may be in the form of a proximally extending member as shown integrally formed with flange 64, or may be in the form of an internal tool recess. Tool engaging portion 66 can be severable on application of a threshold torque to engaging member 60 when rod 12 is seated in receiver 90 of anchor 28. Tool engaging portion 66 can also be fixed and non-removable from body 62. In another embodiment, flange 64 is rotatably captured between tool engaging portion 66 and body 62 so that its relative orientation with connector body 32 is maintained as engaging member 60 is engaged to anchor 28.

When engaging member 60 is positioned to engage connector body 32 against rod 12, it is contemplated that a distal end 68 of threaded body 62 can be spaced from rod 12. This ensures that connector body 32 is firmly engaged by flange 64 and rod 12, thus coupling rod 12 securely to anchor 28. Flange 64 can include an outer perimeter that is rectangular, square, circular or any other suitable shape to contact the proximal surface 48 of connector body 32.

Figure 4:
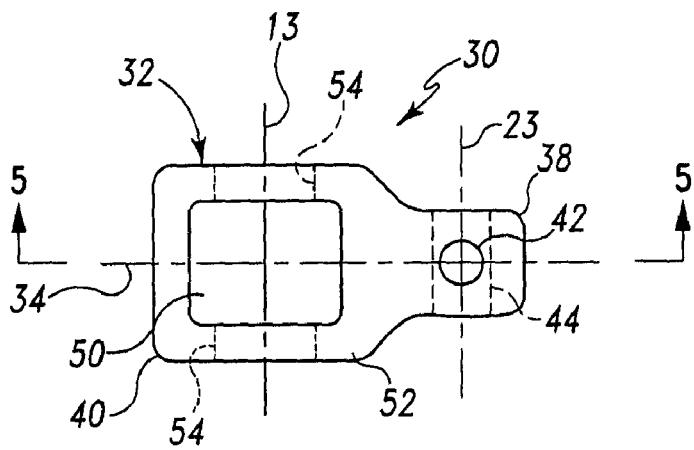
FIG. 4 is a plan view of the connector of FIG. 1.
Figure 5:
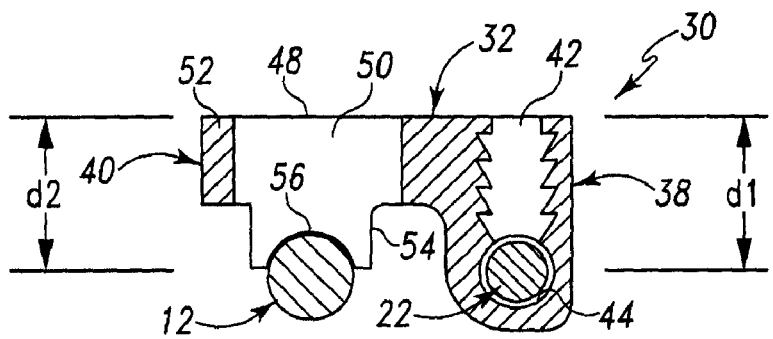
FIG. 5 is a section view of the connector through line 5-5 of FIG. 4 and further showing a pair of rods positioned relative to the connector.
Figure 8:
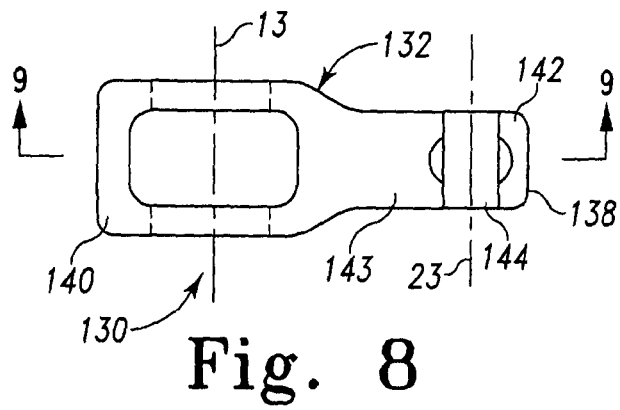
FIG. 8 is a plan view of another embodiment connector.
Figure 9:
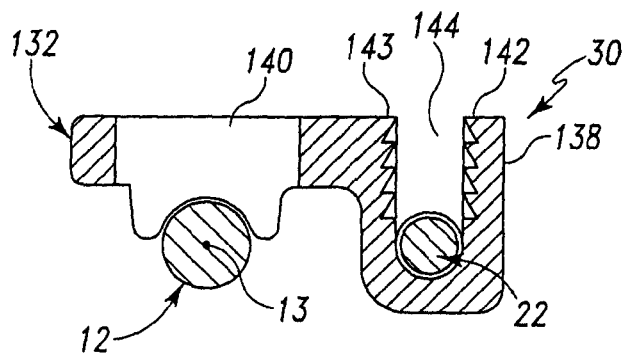
FIG. 9 is a section view of the connector through line 9-9 of FIG. 8 and further showing a pair of rods positioned relative to the connector.

Other embodiments contemplate other configurations for connector 30. For example, FIGS. 8-9 show connector 130 with a connector body 132 having a receiving portion 138 and a mounting portion 140. Mounting portion 140 can be configured like mounting portion 40 discussed above. However, receiving portion 138 includes an open configuration where a pair of arms 142, 143 define a receptacle 144 therebetween for receiving engaging member 80. Rod 22 can be positioned between arms 142, 143 in a side-loading fashion, i.e. from the side of rod 22, and seated in the bottom of receptacle 144. Engaging member 80 can be threadingly engaged to arms 142, 143 into contact with rod 22 to firmly seat and secure rod 22 against receiving portion 138. In the embodiment of FIGS. 4-5, receiving portion 38 was shown with a closed type configuration around bore 42, and thus rod 22 is loaded in an endwise fashion, or end-loaded, into and through receptacle 44.

Figure 10:
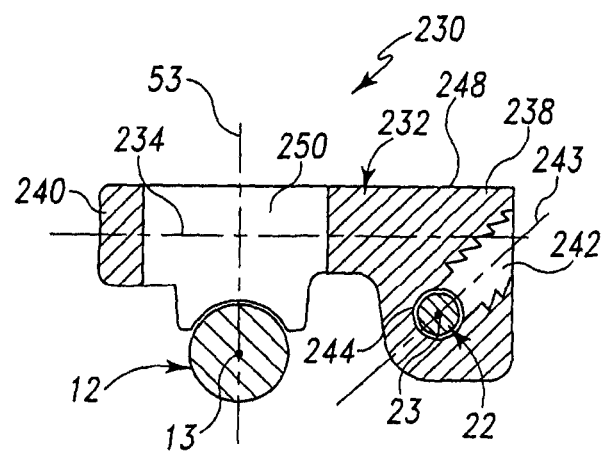
FIG. 10 is a section view of another embodiment connector and pair of spinal rods positioned relative thereto.

FIG. 10 shows another embodiment connector 230 having a connector body 232 with a receiving portion 238 and a mounting portion 240. Mounting portion 240 can be configured like mounting portion 40 discussed above and positioned about mounting anchor 28 and engaged to rod 12 with engaging member 60. Receiving portion 138 includes a bore 242 that extends along an oblique bore axis 243 from receptacle 244. Bore axis 243 is obliquely oriented to an engaging axis 53 along which engaging member 60 engages mounting anchor 28 when viewed in section along longitudinal axis 234 as shown in FIG. 10. In addition, bore axis 243 is obliquely oriented to longitudinal axis 234 of body 232 when viewed in section along longitudinal axis 234 as shown in FIG. 10. In the illustrated embodiment, axis 243 extends from rod 22 through a side of connector body 32 that is remote from rod 12. In another embodiment, bore 242 and thus bore axis 243 extend from receptacle 244 toward window 250 through upper proximal surface 248 of connector body 232.

Rods 12, 22 can be of the same size, shape and material properties, or more have one or more of these characteristics that differ from one another. Connector 30 allows rods of differing characteristics to be secured to one another in laterally offset and axially extending relation for positioning along multiple levels of the spinal column and provide a rod system that is adapted for the anatomy, surgical condition, or surgical procedure. In one embodiment, the characteristics include differing cross-sectional dimensions of the rods 12, 22. Other embodiments contemplate selection criteria for selection and assembly of the rods to include any one or combination of characteristics, including length, contouring, flexibility, surface features, shape, section modulus, elasticity, materials and material properties, and coatings, for example.

In one specific application, the diameter of rod 22 is sized to extend along a first portion of the spine, such as the cervical region, and the diameter of second rod 12 is sized to extend along a second portion of the spine, such as the thoracic region. Other systems contemplate multiple rods coupled to one another in axially offset fashion with characteristics adapted for positioning along any one or combination of the sacral, lumbar, thoracic and cervical regions of the spinal column.

Connector 30 is configured to be secured to rods 12, 22 with rods 12, 22 in side-by-side or near side-by-side relation. When in side-by-side relation, rods 12, 22 can overlap one another in connector 30 in a lengthwise direction. This minimizes the footprint or intrusiveness of connector 30 into the tissue surrounding the rod system, and maximizes the length of the rod portion of each rod available for positioning and/or attachment along the spinal column. The positioning of rods 12, 22 in connector 30 can also be adjusted so that the rods 12, 22 do not directly overlap one another. For example, receiving portion 38 can be offset cephaladly or caudally relative to mounting portion 40 so that the rods do not overlap when engaged to connector 30.

In the embodiments illustrated herein, although only one connector is shown, one or more of the first and second rods can be adapted for engagement with another rod with another connector 30 or other device at each end thereof so that three or more rods may comprise the rod system. The rods can be secured to vertebrae of the spinal column system with anchors that include any one or combination of hooks, screws, bolts, multi-axial screws, staples, cables or wires, sutures, clamps, and/or other attachment devices and systems, with or without interbody fusion devices or implants between vertebrae.

Engaging members 60 and 80 can be positionable in the respective bores of connector 30 either prior to placement of rods 12, 22 in receptacle 94 of anchor 28 and receptacle 44 of connector 30, or after placement or rods 12, 22 in receptacles 90, 44. The engaging members can be in the form of set screws with a proximally oriented tool engaging recess or extension to facilitate engagement with a driving tool. Other embodiments contemplate other arrangements for engagement of connector 30 with the engaging members, such as bayonet locks, friction fits, engagement members that include multiple components.

Figure 11:
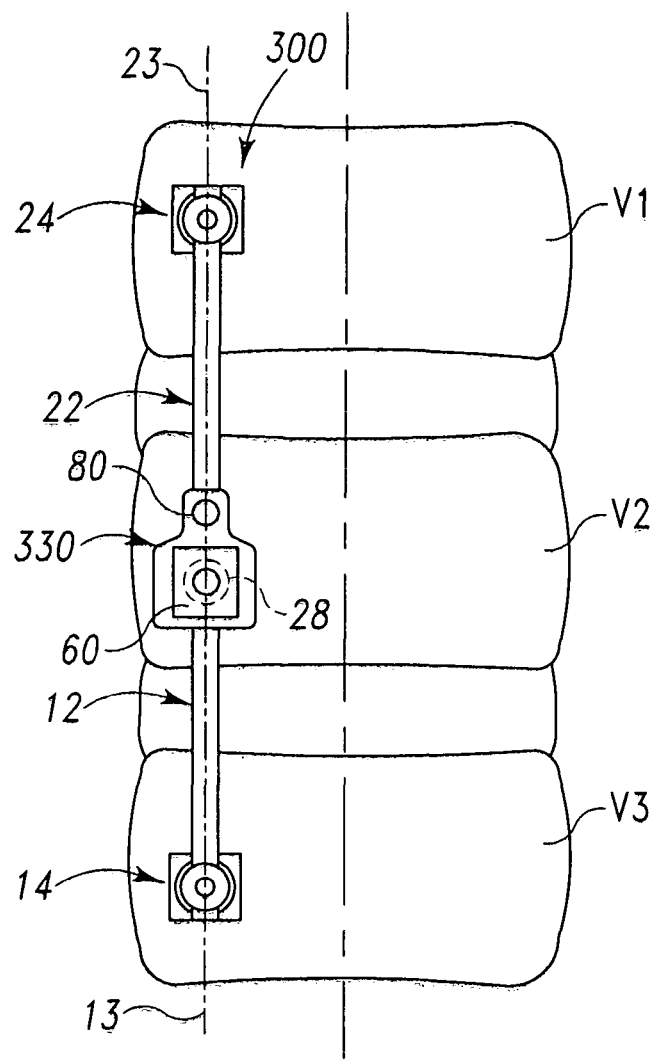
FIG. 11 is an elevation view of a spinal column segment shown diagrammatically and another embodiment of a stabilization system employing another embodiment connector to connect two rods to an anchor.
Figure 12:
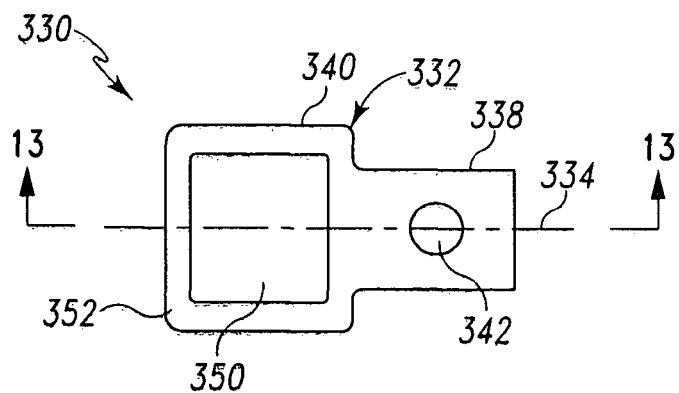
FIG. 12 is a plan view of the connector of FIG. 11.
Figure 13:
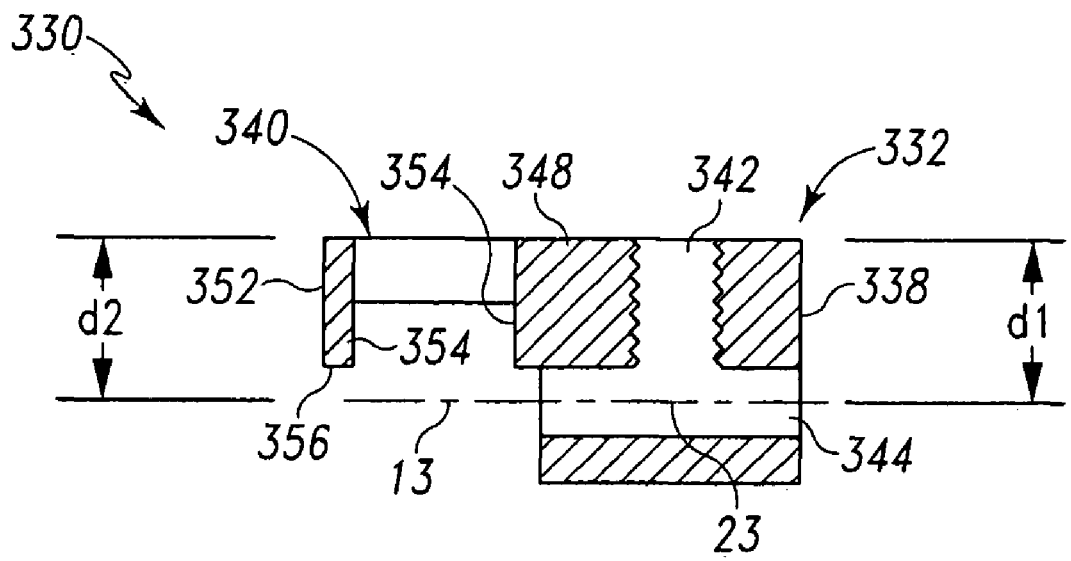
FIG. 13 is a section view of the connector along line 13-13 of FIG. 12.

In FIG. 11 there is shown a spinal rod system 300 including first rod 12 and second rod 22. First rod 12 and second rod 22 are releasably coupled to one another with connector 300 at a mounting anchor with rods 12, 22 in end-to-end relation and in axial alignment with one another when positioned along the spinal column. Rods 12, 22 provide a construct between the respective first and second vertebrae V1 and V2 and the respective second and third vertebrae V2 and V3 to provide a desired stabilization effect. First rod 12 can be secured to at least one vertebra V1 with at least one first anchor 14, and second rod 22 can be secured to at least one third vertebra V3 with at least one third anchor 24. Rods 12, 22 are secured to second, mounting anchor 28 engaged to vertebra V2 to provide spinal rod system 300 along vertebrae V1, V2, V3.

The length of the construct between anchors 14 and 28 and anchors 24 and 28 can be decreased or increased by adjusting the axial positioning of one or more of the rods 12, 22 in the respective mounting anchor 28 and/or rod connector 330. Such adjustment may be desirable, for example, to provide an optimal fit during surgery, to allow rods of shorter length to be assembled in a single system, to allow rods of varying properties to be employed in the same system, and/or to adjust the length of the construct as a result of growth or other changes in the patient anatomy after the initial implantation procedure. In addition, system 300 can be adapted to extend along a single vertebral level, two vertebral levels as shown, or along three or more vertebral levels. System 300 can employ multiple mounting anchors and connectors along with multiple other anchors to secure two or more rods along the spinal column.

Connector 330 includes a connector body 332 releasably engageable to mounting anchor 28 and second rod 22. In addition, connector body 332 is positionable in contact with first rod 12 in mounting anchor 28 to secure first rod 12 to mounting anchor 28. Body 332 of connector 330 also includes a receptacle 344 for receiving second rod 22 therein. Connector 330 is configured to secure rods 12, 22 with rod 12 along rod axis 13 and rod 22 along rod axis 23. Axes 13, 23 can be generally aligned with one another while minimizing the footprint or intrusiveness of the connector into the tissue surrounding the rod system and allowing the length of the rod construct for positioning and/or attachment along the spinal column to be readily adjustable. The rods 12, 22 can extend along their respective axes 13, 23 in opposite directions from rod connector 330 for positioning along one or more spinal motion segments of the spinal column to provide stabilization.

Connector body 332 includes a receiving portion 338 for receiving rod 22 therein and a mounting portion 340 alongside receiving portion 338 for positioning about mounting anchor 28. Connector body 332 extends along a longitudinal axis 334 that is aligned axially with axes 13, 23 of rods 12, 22 when rods 12, 22 are engaged to connector body 332. The width of connector body 332 transverse to longitudinal axis 334 can be less than, the same as, or greater than the length along longitudinal axis 334. In addition, the width transverse to longitudinal axis 334 can vary along its length.

Mounting portion 340 includes a length and width along and transverse to longitudinal axis 334 to accommodate receiver 90 of anchor 38 in window 350. Receiving portion 338 includes a length along axis 334 sufficient to form receptacle 344 for receiving rod 22 therein along rod axis 23. Receiving portion 338 also includes a bore 342 for receiving an engaging member, such as engaging member 80 shown in FIG. 7, to secure rod 22 in position in receptacle 344.

Receiving portion 338 can include a depth d1 from a proximal or upper surface 348 of connector body 332 that positions the centerline 23 of rod 22 in alignment distally and proximally with the depth d2 of the centerline 13 of rod 12 below proximal surface 348. Other embodiments contemplate that depth d1 and depth d2 differ from one another to accommodate, for example, changes in the anatomy of the patient.

Mounting portion 340 of connector body 332 includes a central window 350 to receive receiver 90 of anchor 28 therein, as shown in FIG. 6. Wall 352 extends around window 350 and is shaped like the outer perimeter of anchor 28 so that receiver 90 is received in close, form-fitting engagement therewith. At least one contact member 354 extends distally from or is formed with wall 352 and is positioned in contact with rod 12 outside receptacle 94. Contact member 354 can include a distal contact surface 356 that can be concavely curved to fit around a portion of the convexly curved perimeter of rod 12. It is contemplated that a contact member 354 can be provided on each side of anchor 28 to contact rod 12 outside receptacle 94. The distal contact surface 356 can include any suitable configuration, including configurations that conform to or extend around rods with non-circular outer perimeters. Engaging member 60 is engageable to anchor 28 in receiver 90 so that as engaging member 60 is threadingly advanced into receiver 90, rod 12 is seated against receiver 90 by contact members 354 pressing against rod 12, limiting or preventing further rotation of engaging member 60.

Figure 14:
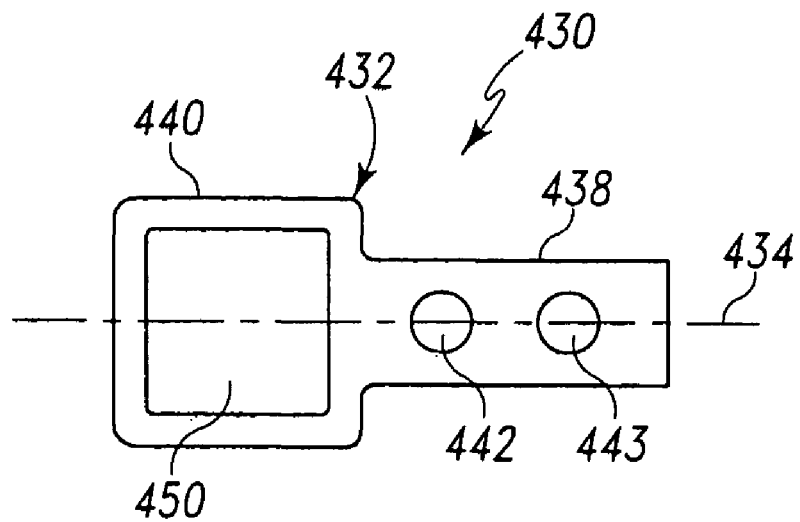
FIG. 14 is a plan view of another embodiment connector.

Other configuration for receiving portion 338 are contemplated. For example, receiving portion 338 can be top-loading and define a space between a pair of arms such as discussed above with respect to receiving portion 138. Bore 342 can be obliquely oriented to the axis 334 or open along a side of receiving portion 338. In FIG. 14 connector 430 is shown with a connector body 432 having a mounting portion 440 defining a window 450 configured like mounting portion 340 of connector 330. Connector 430 includes a receiving portion 438 with first and second bores 442, 443 to receive engaging members, such as engaging members 80 discussed above. Bores 442, 443 can be spaced along longitudinal axis 434 and provide multiple locations along rod 22 for engagement to axially secure rod 22 in connector 430.

While the invention has been illustrated and described in detail in the drawings and foregoing description, the same is to be considered as illustrative and not restrictive in character. All changes and modifications that come within the spirit of the invention are desired to be protected.

What is claimed is:

1. A spinal rod system, comprising:
   a mounting anchor including a first portion engageable to at least one vertebra and a receiver defining a first receptacle;
   a first elongated spinal rod in said receptacle of said mounting anchor, said first spinal rod being positionable along a spinal column and is configured with a length sized to extend from said mounting anchor to at least one other vertebra when said first portion of said mounting anchor is engaged to the at least one vertebra;

a connector including a body extending along a longitudinal axis oriented transversely to said first spinal rod, said body including a mounting portion and a receiving portion along said longitudinal axis, wherein said receiver is positioned within said mounting portion and engaged thereto with an engaging member engaged in said receiver and in contact with said mounting portion outside said receiver so that said mounting portion is pressed into contact with said first spinal rod outside said receiver with said first spinal rod spaced from said engaging member in said first receptacle and said receiving portion of said connector is positioned adjacent said receiver of said mounting anchor, said receiving portion defining a second receptacle; and a second spinal rod engaged to said receiving portion of said connector in said second receptacle and extending from said receiving portion in generally parallel relation with said first spinal rod.

2. The system of claim 1, wherein said first spinal rod extends in a first direction away from said connector and said second spinal rod extends in a second direction away from said connector opposite said first direction.

3. The system of claim 1, wherein said receiver of said mounting anchor includes a pair of arms extending along said first receptacle and said engaging member is threadingly engaged to said pair of arms.

4. The system of claim 3, wherein said engaging member includes a distal threaded body threadingly engaging said pair of arms and a flange proximal of said body positioned in contact with a proximally oriented surface of said body of said connector.

5. The system of claim 4, wherein said connector includes at least one contact member extending therefrom adjacent to said receiver, said contact member including a distal contact surface positioned in contact with said first spinal rod and seating said first spinal rod in said receiver of said mounting anchor.

6. The system of claim 1, wherein said connector includes at least one contact member extending therefrom adjacent to said receiver and outside of said first receptacle of said mounting anchor, said contact member including a distal contact surface positioned in contact with said first spinal rod and seating said first spinal rod in said receiver of said mounting anchor.

7. The system of claim 6, wherein said engaging member contacts a proximally oriented surface of said body of said connector and is movably engageable with said receiver to place said contact surface into contact with said first spinal rod.

8. The system of claim 1, wherein said receiving portion of said connector includes a bore in communication with said second receptacle and a second engaging member in said bore securing said second spinal rod to said body of said connector.

9. The system of claim 8, wherein said bore is defined between a pair of arms extending from said second receptacle along said bore and defining an opening therebetween configured to receive said second spinal rod therethrough in a side-loading orientation.

10. The system of claim 8, wherein said bore extends along a bore axis that is obliquely oriented to said longitudinal axis of said connector when said body of said connector is viewed in section along said longitudinal axis.

11. The system of claim 1, wherein said first portion of said mounting anchor includes an elongated, threaded shaft and said receiver extends proximally from said threaded shaft.

12. A spinal rod system, comprising:

a mounting anchor including a first portion engageable to at least one vertebra and a receiver defining a first receptacle;

a first elongated spinal rod in said receiver of said mounting anchor, said first spinal rod being positionable along a spinal column and is configured with a length sized to extend from said mounting anchor to at least one other vertebra when said first portion of said mounting anchor is engaged to the at least one vertebra;

a connector including a body extending along a longitudinal axis oriented transversely to said first spinal rod, said body including a mounting portion and a receiving portion along said longitudinal axis, wherein said receiver is positioned within said mounting portion so that said mounting portion is clampingly engaged against said first spinal rod outside said first receptacle with an engaging member engaged within said receiver of said mounting anchor and in contact with said mounting portion outside said receiver, wherein said spinal rod is spaced from said engaging member in said first receptacle, and further wherein said receiving portion of said connector defines a second receptacle adjacent said mounting portion; and a second spinal rod engaged to said receiving portion of said connector in said second receptacle and extending from said receiving portion in generally parallel relation with said first spinal rod.

13. The system of claim 12, wherein said mounting portion includes a wall that extends around and defines a window, and said receiver of said mounting anchor is received in said window in form-fitting and non-rotating engagement therewith.

14. The system of claim 13, wherein said mounting portion includes at least one contact member along said wall, said at least one contact member including a distal surface contacting said first spinal rod outside said first receptacle of said receiver of said mounting anchor.

15. The system of claim 14, wherein said contact surface includes a concave curvature to extend at least partially around a convex outer surface of said first spinal rod.

16. The system of claim 12, wherein said engaging member includes a distal threaded body threadingly engaging said receiver and a flange extending about said body proximally thereof that is positioned in contact with a proximally oriented surface of said body of said connector.

17. The system of claim 12, wherein said receiving portion of said connector includes a bore in communication with said second receptacle and a second engaging member in said bore securing said second spinal rod to said body of said connector.

18. The system of claim 12, wherein said first spinal rod extends along a central axis located a first depth below a proximal-most surface of said connector body and said second spinal rod extends along a second axis located a second depth below said proximal-most surface, wherein said first depth is substantially the same as said second depth.

19. The system of claim 12, wherein said first portion of said mounting anchor includes an elongated, threaded shaft and said receiver extends proximally from said threaded shaft, said receiver includes a U-shaped head having a pair of arms extending alongside one another and defining said first receptacle therebetween.

20. A method for assembling a spinal rod system, comprising:

positioning a first spinal rod into a first receptacle defined by a receiver of a mounting anchor;

positioning the receiver of the mounting anchor within a mounting portion of a connector body;

securing an engaging member to the receiver of the mounting anchor with a flange of the engaging member in contact with the connector body outside the first receptacle and the connector body in contact with the first spinal rod outside the first receptacle;

advancing the engaging member into the receiver thereby advancing the connector body and spinal rod in contact therewith until the spinal rod is seated against the receiver of the mounting anchor with the first spinal rod spaced from both the engaging member and the connector body in the first receptacle; and engaging a second spinal rod to the connector body with the second spinal rod extending from the connector body in a direction opposite to the first spinal rod with the second spinal rod aligned in a generally axial alignment with the first spinal rod.

21. The method of claim 20, wherein the second spinal rod extends from the first spinal rod in end-to-end relation and in generally axial alignment therewith.

22. The method of claim 20, wherein the receiving portion of the connector body is positioned adjacent the receiver when the connector body is positioned about the receiver of the mounting anchor.

23. The method of claim 20, wherein advancing the engaging member includes threadingly engaging the engaging member along a threaded profile extending along the receiver.

24. The method of claim 20, wherein the connector body includes at least one contact member extending to a distal contact surface in contact with the first spinal rod, the distal contact surface including a concave curvature to conform to an outer surface profile of the first spinal rod.

25. The method of claim 20, wherein engaging the second spinal rod includes positioning the second spinal rod in a second receptacle defined by a receiving portion of the connector body, and further comprising advancing a second engaging member into a bore of the receiving portion to secure the second spinal rod thereto.

26. A spinal rod system, comprising:
a mounting anchor including a first portion engageable to at least one vertebra and a receiver defining a first receptacle;
a first elongated spinal rod in said receptacle of said mounting anchor, said first spinal rod being positionable along a spinal column and is configured with a length sized to extend from said mounting anchor to at least one other vertebra when said first portion of said mounting anchor is engaged to the at least one vertebra;
a connector including a body extending along a longitudinal axis oriented in general alignment with said first spinal rod, said body including a mounting portion and a receiving portion along said longitudinal axis, wherein said receiver is positioned within said mounting portion and engaged thereto with an engaging member positioned in said receiver and in contact with said mounting portion outside said first receptacle of said receiver so that said mounting portion contacts said first spinal rod outside said first receptacle while said first spinal rod is spaced from said engaging member and said mounting portion in said first receptacle of said receiver, wherein said receiving portion of said connector is positioned adjacent said receiver of said mounting anchor, said receiving portion defining a second receptacle; and a second spinal rod engaged to said receiving portion of said connector in said second receptacle and extending from said receiving portion in end-to-end relation with said first spinal rod and in axial alignment therewith.

27. The system of claim 26, wherein said receptacle of said receiving portion extends along said longitudinal axis and said receiving portion includes at least one bore in communication with said second receptacle, and further comprising a second engaging member in said at least one bore in engagement with said second rod in said second receptacle.

28. The system of claim 26, wherein said receptacle of said receiving portion extends along said longitudinal axis and said receiving portion includes a pair of bores spaced along said longitudinal axis and in communication with said second receptacle, and further comprising a second engaging member in each of said pair of bores, each of said second engaging members in engagement with said second rod in said second receptacle.

29. The system of claim 26, wherein said receiver of said mounting anchor includes a pair of arms extending along said first receptacle and said engaging member is threadingly engaged to said pair of arms.

30. The system of claim 29, wherein said engaging member includes a distal threaded body threadingly engaging said pair of arms and a flange proximal of said body positioned in contact with a proximally oriented surface of said body of said connector.

31. The system of claim 30, wherein said connector includes at least one contact member extending therefrom adjacent to said receiver, said contact member including a distal contact surface positioned in contact with said first spinal rod and seating said first spinal rod in said receiver of said mounting anchor.

32. The system of claim 26, wherein said connector includes at least one contact member extending therefrom adjacent to said receiver and outside of said first receptacle of said mounting anchor, said contact member including a distal contact surface positioned in contact with said first spinal rod and seating said first spinal rod in said receiver of said mounting anchor.

33. The system of claim 32, wherein said engaging member contacts a proximally oriented surface of said body of said connector and is movably engageable with said receiver to place said contact surface into contact with said first spinal rod.

34. The system of claim 26, wherein said mounting portion includes a wall that extends around and defines a window, and said receiver of said mounting anchor is received in said window in form-fitting and non-rotating engagement therewith.

35. The system of claim 34, wherein said mounting portion includes first and second contact members along said wall on opposite sides of said window, said first and second contact members each including a distal surface contacting said first spinal rod outside said first receptacle of said receiver of said mounting anchor.

36. The system of claim 26, wherein said first portion of said mounting anchor includes an elongated, threaded shaft and said receiver extends proximally from said threaded shaft, said receiver includes a U-shaped head having a pair of arms extending alongside one another and defining said first receptacle therebetween.

* * * * *

UNITED STATES PATENT AND TRADEMARK OFFICE
CERTIFICATE OF CORRECTION

| | |
|---|---|
| PATENT NO. | : 7,867,255 B2 |
| APPLICATION NO. | : 11/399927 |
| DATED | : January 11, 2011 |
| INVENTOR(S) | : Miller et al. |

It is certified that error appears in the above-identified patent and that said Letters Patent is hereby corrected as shown below:

In Column 11, Lines 12-13, in Claim 20, delete "both the engaging member and the connector body" and insert -- the engaging member --, therefor.

In Column 11, Lines 60-61, in Claim 26, delete "engaging member and said mounting portion" and insert -- engaging member --, therefor.

Signed and Sealed this
Twenty-sixth Day of April, 2011

David J. Kappos
*Director of the United States Patent and Trademark Office*